(12) United States Patent
Pierri et al.

(10) Patent No.: US 8,632,025 B2
(45) Date of Patent: Jan. 21, 2014

(54) SYSTEM AND METHOD FOR GROUND MATERIAL CHARACTERIZATION IN A GRINDING SYSTEM

(75) Inventors: Dario Pierri, St. Gallen (CH); Martin Heine, Seuzach (CH); Urs Dübendorfer, Niederuzwil (CH)

(73) Assignee: Bühler AG, Uzwil (CH)

( * ) Notice: Subject to any disclaimer, the term of this patent is extended or adjusted under 35 U.S.C. 154(b) by 367 days.

(21) Appl. No.: 12/992,413

(22) PCT Filed: May 14, 2009

(86) PCT No.: PCT/EP2009/055877
§ 371 (c)(1),
(2), (4) Date: Feb. 22, 2011

(87) PCT Pub. No.: WO2009/138479
PCT Pub. Date: Nov. 19, 2009

(65) Prior Publication Data
US 2012/0002037 A1    Jan. 5, 2012

(30) Foreign Application Priority Data
May 14, 2008 (DE) .......................... 10 2008 001 749

(51) Int. Cl.
*B02C 1/10* (2006.01)
(52) U.S. Cl.
USPC ............................ 241/25; 241/101.2; 241/235

(58) Field of Classification Search
USPC ..................................... 241/25, 30, 101.2, 235
See application file for complete search history.

(56) References Cited

U.S. PATENT DOCUMENTS

| | | | |
|---|---|---|---|
| 4,421,772 A | 12/1983 | Munck et al. | |
| 4,444,457 A | 4/1984 | Studer | |
| 2002/0170367 A1 | 11/2002 | Lieber et al. | |
| 2003/0029946 A1* | 2/2003 | Lieber et al. | 241/34 |
| 2007/0205312 A1* | 9/2007 | Pierri et al. | 241/6 |
| 2009/0206286 A1* | 8/2009 | Pierri et al. | 250/576 |

FOREIGN PATENT DOCUMENTS

| | | |
|---|---|---|
| DE | 4339285 | 6/1994 |
| JP | 58-92807 | 6/1983 |
| JP | 5-66190 | 3/1993 |
| JP | 11-190697 | 7/1999 |
| JP | 2003-294641 | 10/2003 |
| JP | 2007-313467 | 12/2007 |
| WO | 02/44692 | 6/2002 |
| WO | 2006/000112 | 1/2006 |
| WO | 2006/116882 | 11/2006 |

* cited by examiner

*Primary Examiner* — Faye Francis
(74) *Attorney, Agent, or Firm* — Shoemaker and Mattare

(57) ABSTRACT

A stream of ground particles is characterized by irradiating it with electromagnetic radiation and detecting electromagnetic radiation emitted from the irradiated particles. The detecting system includes an imaging system and a color image sensor for imaging the particles by way of the electromagnetic radiation emitted by the particles. The color image sensor has sensor image elements for spectrally selective detection of the electromagnetic radiation.

19 Claims, 3 Drawing Sheets

SYSTEM AND METHOD FOR GROUND MATERIAL CHARACTERIZATION IN A GRINDING SYSTEM

The invention relates to a system and to a method for the characterization of grinding material in a grinding plant, in particular for characterizing particles in a grinding material stream of cereal grinding products in a cereal grinding plant.

In general, the grinding material stream first passes through a cleaning stage, in which foreign bodies, impurities and qualitatively poor grinding material such as brokens or infected grain are removed from the grinding material to be cleaned by way of mechanical, aerodynamic and/or optical separation or sorting processes. This requires a compromise to be struck between the purity and the yield of the cleaned grinding material. The sieves and sieve parameters, air flows and/or optical separating criteria are set such that as little "good" grinding material as possible is removed during the cleaning, while still achieving sufficient quality of the cleaned grinding material. It is therefore desirable for incoming grinding material, the cleaned grinding material and/or the grinding material that has been removed during cleaning to be characterized. If the removed grinding material stream contains too much good grinding material or if the grinding material quality is over specification, the separation intensity is reduced, with the inverse procedure being used if the quality of the grinding material after cleaning is too low. It is possible to assess the quality of the incoming grinding material from its characterization, and to arrive at a prognosis for selecting good separation cuts.

During grinding of granular material, such as wheat, in a comminution machine such as a roller mill, the granular material is comminuted between the rollers of a pair of rollers. In order to yield flour of a specific fineness and material composition, the grinding material must generally be passed several times through such a passage, wherein agglomerates are in the meantime broken up by impact separation and classifications by air-flow sifting and sieving are carried out. It is possible in this manner to obtain flours of varying fineness or varying degrees of grinding.

The grinding effect of a passage is primarily dependent on the nip spacing between the two rollers of a pair of rollers, the speed and the speed ratio of the rollers. However, other roller mill operating parameters or roller mill properties also influence the grinding effect of a passage, such as for example the geometry and wear of the roller surface. It is therefore desirable to obtain characterization of the grinding material that exits after a specific passage. If the grinding material here deviates from a predetermined grinding material characteristic, it is possible on the basis of said deviation to correct the nip spacing, the speed ratio or any other roller mill operating parameters in order to compensate for the deviation as quickly as possible. In addition, it is also possible to detect the maintenance requirements of a roller mill component, if for example the predetermined characteristic can no longer be obtained in a meaningful manner due to a greatly worn roller.

WO2006/116882A1 describes a system and a method for characterizing a particle stream, wherein the form, the dimensions or the movement behavior of the individual particles is detected. In particular, image information of the grinding material stream is obtained, from which the particle size distribution of the grinding material stream is determined. This particle size distribution can then be used to control or regulate a roller mill.

The invention is based on the object of providing a system and a method which enables an even further reaching and more significant characterization of a grinding material stream in a grinding plant, wherein in particular a significant characterization of particles in a grinding material stream of whole cereal grain, cereal intermediate grinding products and cereal end products in a cereal grinding plant is intended to be made possible.

This object is achieved by way of the system and the method according to the independent claims.

The system according to the invention for the characterization of grinding material in a grinding plant has (1.) an irradiation section for passing through at least one part of the grinding material stream and with an irradiation means for irradiating the particles in the at least one part of the grinding material stream using electromagnetic radiation; and (2.) a detection section for passing through the at least one part of the grinding material stream and with a detection means for detecting electromagnetic radiation emitted by particles of that part of the grinding material stream which is conveyed through the irradiation section. According to the invention, the detection means contains an imaging system and a color image sensor for imaging the particles onto the color image sensor using the electromagnetic radiation they reflect or emit, wherein the color image sensor has sensor pixels for the spectrally selective detection of the electromagnetic radiation imaged onto the sensor pixels.

This enables the use of "color information" for the characterization of the particles of the grinding material stream, in that the particles are imaged onto a color image sensor using the electromagnetic radiation they emit, which color image sensor then spectrally selectively detects the electromagnetic radiation on its sensor pixels. "Color information" within the context of the present invention does not only mean color in the narrow meaning, but also spectral information outside the visible spectrum, especially in the UV range and in the IR range.

The characterization using particle size distribution can thus be presented by means of a further dimension of the characterization on the basis of color information. This is advantageous especially in the assessment of the grinding result of cereals because the brokens which originate from various regions of a cereal grain have different colors or differing emission behaviors with respect to the irradiation of specific electromagnetic radiation (IR, visible light, UV). For example, cereal grain brokens or grinding products originating from the endosperm are lighter in color and rather white to yellow, parts of the germ of the cereal grain are rather yellow to green and the cereal grain brokens originating from the husk region are dark and rather brownish.

It is often, for example, the intention during the grinding of wheat to prevent the entire wheat grain being randomly comminuted to small particles, which consist only of endosperm, only of husk parts or are endosperm/husk part mixed particles. In particular it is attempted to achieve selective comminution of the wheat grain or of another cereal grain, with the result that the pure endosperm particles are predominantly, or on average, rather small and approximate a "spherical" or "block" form and the husk parts are predominantly, or on average, rather large and approximate a "plate" form. Such selective comminution simplifies fractionation of the grinding material in a subsequent fractionation step, as a result of which the entire grinding process can be made more efficient, i.e. comminution and subsequently simpler sorting/fractionation not only by size but also by form of the cereal brokens. This enables not only the production of various end products such as bran, grits, flour or germs, but also variations in the end product composition, for example with respect to fiber, mineral, protein and/or fat content.

Owing to the use of particle size information and particle color information according to the invention, it is possible to more appropriately assess the selectivity of the comminution and/or separation process than if only particle size information were used.

For the abovementioned example of the comminution of wheat, this means that, with high selectivity of the comminution process, practically only pure endosperm particles and husk parts with only little adhering endosperm are obtained, while, with low selectivity, many endosperm/husk part mixed particles and only few pure endosperm particles and few husk parts with only little adhering endosperm are obtained.

With reference to the present invention, high selectivity for the wheat comminution is present if in the particle size spectrum the small particles have a light color or are white to yellow (endosperm fraction) and the large particles are dark or gray to brownish (husk parts).

Using color information, it is possible to infer the quantitative composition of the particles by means of image processing. Said color information can be linked with the particle size information, as a result of which particle size distribution of pure husk parts (dark or gray to brownish), particle size distribution of mixed parts with specific proportions of components and particle size distribution of pure endosperm parts can be obtained. This linked information provides a relationship between color information and particle size information and can be used to control and/or regulate the process. If, for example, the proportion of the mixed parts increases, or the size of the husk particles decreases, the nip spacing in the grinding, a change in the moisture in the cereal or a worn surface of the rollers might be the cause. By evaluating measurement data stored in the past and evaluating them with respect to the relationship between particle color information and particle size, the cause of the errors can be localized to a great degree. It is also possible to link further particle properties such as particle surface area content, particle contour properties, particle form factors and particle speeds with the color information in order to make detailed statements relating to the product and the operational state of a machine or plant. The color image sensor can also be used in combination with other measurement methods such as NIR, MIR or IR measurement, UV measurement, inductive and/or capacitive measurement methods.

On the delivery outlet side of the irradiation section, a deagglomeration section for deagglomerating grinding material agglomerates in the grinding material stream is preferably provided. This prevents agglomerates from a plurality of grinding material particles from being erroneously detected and identified as large grinding material particles. Preferably, the particles in the deagglomeration section are accelerated in an air flow and singulated by the fluid mechanical shear forces which occur in the process. Ideally, cereal grinding intermediate and end products are fed to the detection section at speeds of >10 m/s and whole cereal grains at 1-10 m/s.

The detection section can be arranged downstream of the irradiation section along the direction of the grinding material stream. This is advantageous especially if a distinct difference in the spectrum emitted by the particles occurs only with a certain delay after the irradiation of the particles with a predetermined spectrum or a predetermined frequency (or wavelength). For example, the dark husk parts tend towards a stronger emission in the IR range after irradiation with visible light than the lightly colored endosperm particles.

The detection section and the irradiation section can also be arranged at the same location along the direction of the grinding material stream. This permits a compact design of the apparatus according to the invention.

The detection section preferably has two opposing walls, between which a gap is formed through which the at least one part of the grinding material stream can be passed, wherein the two opposing walls are preferably plane surfaces which are arranged mutually parallel. The detection means is preferably directed into the gap.

Expediently, the opposing walls of the detection section are permeable to electromagnetic radiation which can be detected by the color image sensor. Thus the color image sensor can optionally be arranged on either side of the gap behind one of the walls. In addition, when an irradiation unit is mounted on both sides of the gap of the detection section, it is possible for combined illumination with reflected and transmitted light to combine the advantages of both illumination methods. In this case, preferably telecentric irradiation of the grinding material in transmitted light is used to image the contour of the shade of even small grinding material particles exactly on the color image sensor, while obliquely incident reflected light at an angle of preferably at least 45° to the vertical is used to detect the associated particle color information. As a result, sharper contours than in the case of only reflected light illumination, but also color information can be detected as opposed to only transmitted light illumination.

Preferably, the first wall of the two opposing walls of the detection section is permeable to electromagnetic radiation which can be detected by the color image sensor, while the second wall is impermeable to electromagnetic radiation which can be detected by the color image sensor and is more absorptive than the grinding material particles. In this arrangement, the color image sensor is arranged on one side of the gap on the outlet side of the gap on the permeable wall, and a source for electromagnetic radiation, in particular a light source, for the electromagnetic radiation which can be detected by the color image sensor is arranged on the same side of the gap on the outlet side of the gap on the permeable wall. As a result, the grinding material of the grinding material sample conveyed through the gap can be irradiated, and the scattered light or the reflection of the particles of the grinding material sample passes into the field of view of the color image sensor. In this arrangement, a telecentric objective with telecentric reflected light illumination is preferably used to be able to detect to scale grinding material particles in the entire range of depth of field.

Expediently, the detection means is arranged on one side of the gap on the outlet side of the gap on the permeable wall, and the irradiation means is arranged on the same side of the gap on the outlet side of the gap on the permeable wall, so that the particles of the grinding material stream conveyed through the gap are irradiated.

The gap-side surface of the second wall preferably has a stronger absorption of the electromagnetic radiation emitted by the irradiation means than the surfaces of the particles of the grinding material stream. This ensures that there is sufficient contrast between the reflective grinding material particles, which move in front of the gap-side surface, and the radiation reflected by the wall so that the imaged grinding material particles can be detected effortlessly and the subsequent image processing is considerably easier. This saves complicated and time-consuming filter processes during image processing.

The two opposing walls can each be assigned one cleaning apparatus, with which the two opposing walls can be freed of adhering grinding material particles. The cleaning apparatus can be a vibration source, in particular an ultrasound source, which is connected in each case rigidly to the two opposing walls so as to be able to cause the two walls to vibrate. This ensures that not too many resting grinding material particles, i.e. particles which adhere to the one or the other wall, are imaged onto the color image sensor. The particle size distribution of the grinding material particles adhering to the walls is typically different than that of the grinding material particles entrained in the grinding material stream. If the desire is to proceed without distinguishing between resting and moving grinding material particles in the detection and processing of the grinding material stream image information, such wall cleaning should therefore be carried out regularly in order to "shake off" the particles adhering to the walls. A suitable cleaning apparatus is a vibration source, in particular an ultrasound source, with which the gaseous medium between the two opposing walls can be caused to vibrate.

The irradiation section and the detection section are preferably arranged downstream of a comminution unit and/or downstream of a fractionation unit of the grinding plant, with the comminution unit being a roller mill in particular. In this case, a first irradiation and detection section is preferably arranged in the region of the first axial end of the roller mill and a second irradiation and detection section is arranged in the region of the second axial end of the roller mill. It is thus possible to obtain information relating to the degree of grinding as a function of the axial position along the pair of rollers. In the case of non-symmetrical grinding material characteristics along the pair of rollers or in particular between the left-hand and the right-hand end regions of the roller passage, it is possible to reach conclusions relating to misalignment of the rollers of the pair of rollers and to take corrective action.

The system preferably has an image processing system for processing images originating from the color image sensor. This image processing system preferably has means in order to distinguish in the case of the grinding material particles detected and imaged by the color image sensor (in particular in the reflection or transmitted light mode) between moving grinding material particles and grinding material particles adhering to the walls. To this end, it is possible for example by way of repeat detection of a particle in one or in two successive images to detect its speed. Alternatively, it is also possible by way of analysis at least of the last two images to detect resting particles. In that case, the resting grinding material particles adhering to the wall can remain excluded in the evaluation during image processing, so that only the moving grinding material particles are used for evaluation. As a result, incorrect results relating to the particle size distribution of the grinding material are avoided.

Before and/or during the passage of the at least one part of the grinding material stream through the detection section, deagglomeration of grinding material agglomerates in the grinding material stream preferably takes place. During and/or after the passage of the at least one part of the grinding material stream through the detection section, the images imaged onto the color image sensor are preferably processed. Irradiation of the particles, detection of the radiation emitted by the particles and processing of the images imaged onto the color image sensor can be continuous, wherein especially the irradiation of the particles can be carried out in the manner of a stroboscope by way of a series of flashes of light.

In order to enable continuous processing of the images imaged onto the color image sensor, the system ideally has a preferably integrated computing unit, such as a DSP (digital signal processor) and/or FPGA (field programmable gate array), in order to be able to process even higher image rates of preferably >15 images per second. The computing unit reduces the amount of data detected by the color image sensor and classifies said data with respect to the measured particle properties such as particle color proportions, particle size, particle contour, particle form and/or particle speed in histograms which represent the statistically relevant information. This information is then accumulated preferably over measurement times of one second to five minutes and then transmitted to a device for process monitoring, control or regulation or to a data memory.

The images imaged onto the color image sensor of the at least one part of the grinding material stream can be used to regulate the grinding plant, specifically to regulate a comminution unit and/or a fractionation unit in the grinding plant.

The invention makes it possible to distinguish, in addition to particle size, particle form and possibly other properties such as particle speed, the colors of the various particles consisting of the main components of the cereal grain. It is thus possible to determine the respective color-specific particle size distribution for the differently colored main components of the cereal grain (endosperm, husk, germ). As a result, a significant insight into the comminution and fractionation result of a comminution and fractionation step in a grinding method is obtained, with the result that it is possible to optimize the grinding process online and to set the optimum operating state for respectively different raw materials and environmental conditions.

By using two or more detection means per irradiation section, the time it takes to obtain a sufficiently exact particle size statistic can be shortened significantly. The detection means here preferably have image sections of different size. It is possible in this case to use one irradiation means for one or more detection means.

The invention will be explained below using diagrammatic figures, without restricting the subject matter of the invention to the embodiments shown therein.

Figure 1:
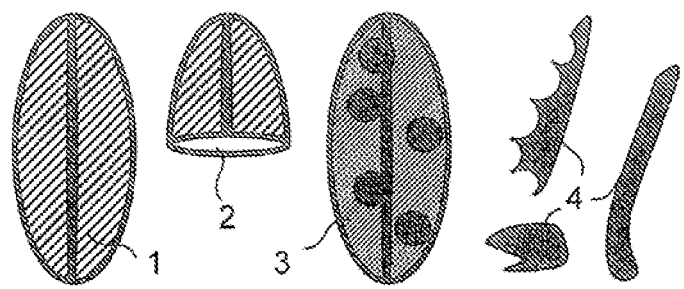
FIG. 1 is a diagram of cereal grain and foreign bodies.

FIG. 1 shows a whole cereal grain 1, and a broken cereal grain 2, an infected cereal grain 3 and foreign bodies 4. Husk parts of the cereal grain are rather dark (gray to brownish), whereas the endosperm is rather lightly colored (white to yellowish), which is indicated at the break edge of the broken cereal grain 2. Infections of the grain are rather dark.

Figure 2:
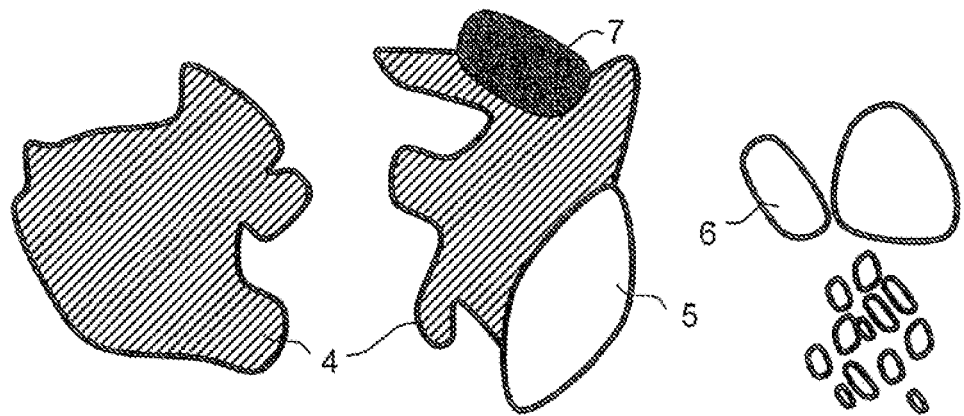
FIG. 2 is a diagram of grinding products.

FIG. 2 shows a diagram of the typical comminution products obtained during grinding of a cereal grain: a pure husk part 4 and husk parts with still adhering endosperm and possibly still with the germ 7. Preferred grinding products are purely spherical or block-shaped endosperm particles 6.

Figure 3:
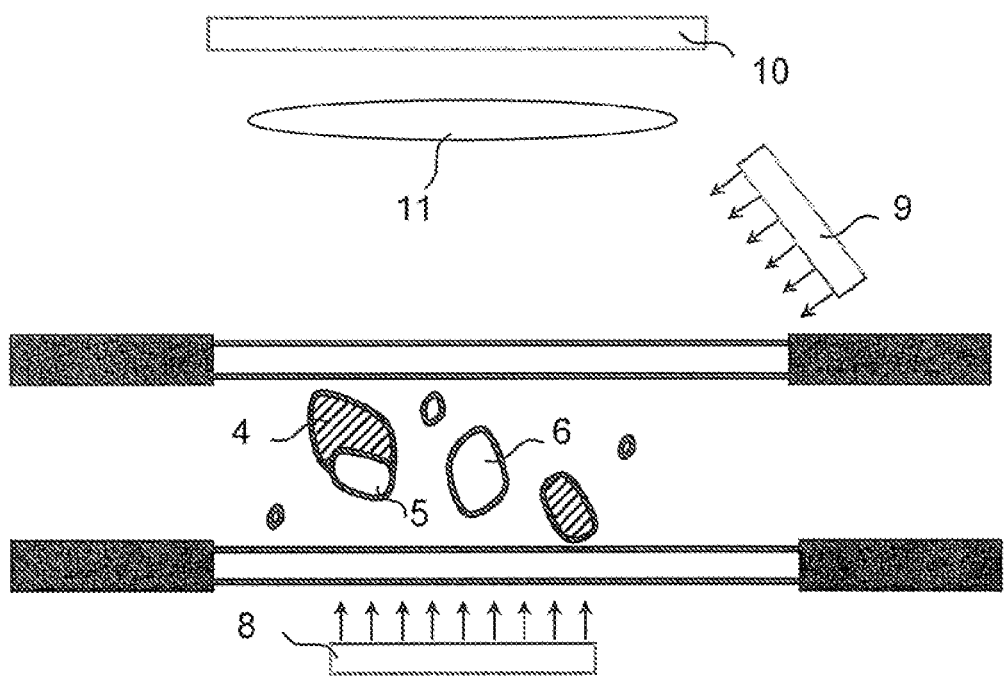
FIG. 3 is a diagram of a first system according to the invention.

FIG. 3 shows a diagram of an embodiment of the system according to the invention for characterizing particles in a grinding material stream of cereal grinding products in a cereal grinding plant. In this exemplary embodiment, irradiation section and detection section are arranged at the same height of the gap through which the grinding material stream is passed. The various grinding products (4, 5; 6) pass through a gap and are irradiated with electromagnetic radiation (in this case transmitted light) via an irradiation unit 8. The grinding products (4, 5; 6) which were irradiated in such a manner in turn emit electromagnetic radiation that is guided, via a lens or a lens system 11, onto a color image sensor 10 and detected thereby. Especially preferred is a combination of transmitted light (produced using the irradiation unit 8) and reflected light, which is aligned at an acute angle to the grinding material stream; this is illustrated by the illumination unit 9.

Figure 4:
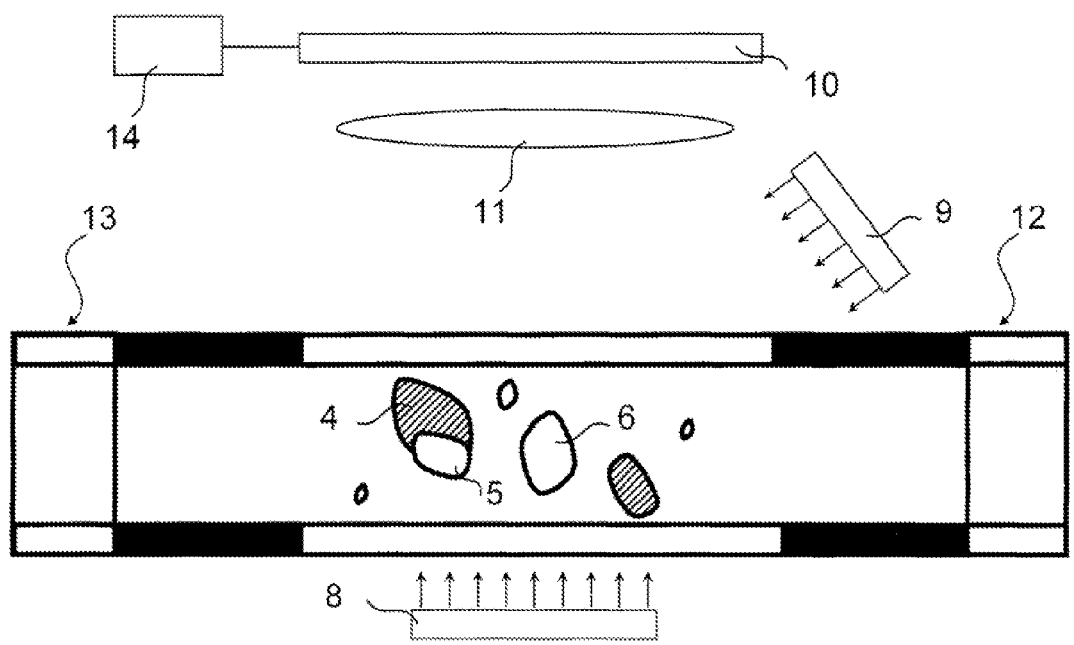
FIG. 4 is a diagram of a second system according to the invention.

The second embodiment shown in FIG. 4 additionally contains a deagglomeration section 12 for deagglomerating grinding material agglomerated in the grinding material stream, which is arranged on the delivery outlet side of the irradiation section. Moreover, the second embodiment also contains a roller mill 13, wherein the irradiation section and the detection section are arranged downstream of the roller mill 13. Furthermore, the second embodiment also comprises a computing unit 14, with which the image information can be evaluated continuously.

The invention claimed is:

1. A system for the characterization of grinding material in a grinding plant, the system having:
    an irradiation section for passing through at least one part of the grinding material stream, wherein the irradiation section has at least one irradiation means for irradiating particles in the at least one part of the grinding material stream using electromagnetic radiation; and
    a detection section for passing through the at least one part of the grinding material stream, wherein the detection section has at least one detection means for detecting electromagnetic radiation emitted by particles of that part of the grinding material stream which is conveyed through the irradiation section;
    wherein the detection means has an imaging system and a color image sensor, adapted such that the particles can be imaged onto the color image sensor using the electromagnetic radiation they emit,
    wherein the color image sensor has sensor pixels for the spectrally selective detection of the electromagnetic radiation imaged onto the sensor pixels and the detection section comprises at least one illuminant or a combination of illuminants, which is/are configured and arranged such that the grinding material particles can be detected with a combination of transmitted light and reflected light.

2. The system as claimed in claim 1, for characterizing particles in a grinding material stream of cereal grinding products in a cereal grinding plant.

3. The system as claimed in claim 1, wherein, on the delivery outlet side of the irradiation section, a deagglomeration section for deagglomerating grinding material agglomerates in the grinding material stream is provided.

4. The system as claimed in claim 1, wherein the detection section and the irradiation section are arranged at the same location along the direction of the grinding material stream.

5. The system as claimed in claim 1, wherein the irradiation section and the detection section are arranged downstream of a comminution unit and/or downstream of a fractionation unit and/or downstream of a cleaning unit of the grinding plant.

6. The system as claimed in claim 5, wherein the comminution unit is a roller mill.

7. The system as claimed in claim 6, wherein a first irradiation and detection section is arranged in the region of the first axial end of the roller mill and a second irradiation and detection section is arranged in the region of the second axial end of the roller mill.

8. The system as claimed in claim 1, wherein it comprises a computing unit, with which the image information can be evaluated continuously and the individual particle information or statistics obtained can be transmitted to a process or machine monitoring apparatus, controller, regulator and/or to a data memory.

9. The system as claimed in claim 8, wherein the individual particle information or statistics obtained can be transmitted to a process or machine monitoring apparatus, controller, regulator and/or to a data memory in defined time intervals.

10. The system as claimed in claim 1, wherein the detection section comprises at least one illuminant or a combination of illuminants, which is/are configured and arranged such that the grinding material particles can be detected with in particular telecentric reflected light.

11. The system as claimed in claim 1, wherein the reflected light is aligned in particular at an acute angle to the grinding material stream.

12. A method for the characterization of grinding material in a grinding plant, the method having the following steps:
    passing at least one part of the grinding material stream through an irradiation section and irradiating the particles in the at least one part of the grinding material stream using electromagnetic radiation; and
    passing the at least one part of the grinding material stream through a detection section and detecting electromagnetic radiation emitted or reflected by particles of that part of the grinding material stream which is conveyed through the irradiation section;
    wherein the particles are imaged onto a color image sensor using the electromagnetic radiation they emit, which color image sensor spectrally selectively detects the electromagnetic radiation on its sensor pixels, and
    wherein the grinding material particles are detected with a combination of transmitted light and reflected light.

13. The method as claimed in claim 12, for characterizing particles in a grinding material stream of cereal grinding products in a cereal grinding plant.

14. The method as claimed in claim 12, wherein before and/or during the passage of the at least one part of the grinding material stream through the detection section, deagglomeration of grinding material agglomerates in the grinding material stream takes place.

15. The method as claimed in claim 12, wherein during and/or after the passage of the at least one part of the grinding material stream through the detection section, the images imaged onto the color image sensor are processed.

16. The method as claimed in claim 12, wherein irradiation of the particles, detection of the radiation emitted by the particles and processing of the images imaged onto the color image sensor are carried out continuously.

17. The method as claimed in claim 16, wherein the irradiation of the particles is carried out in the manner of a stroboscope by way of a series of flashes of light.

18. The method as claimed in claim 12, wherein the images imaged onto the color image sensor of the at least one part of the grinding material stream are used to control or regulate the grinding plant.

19. The method as claimed in claim 18, wherein the images imaged onto the color image sensor of the at least one part of the grinding material stream are used to regulate a comminution unit and/or a fractionation unit in the grinding plant.

* * * * *